(12) United States Patent
Jackson, III

(10) Patent No.: US 7,883,130 B2
(45) Date of Patent: Feb. 8, 2011

(54) SURGICAL MAGNETIC RETRIEVAL TOOL

(76) Inventor: Avery M. Jackson, III, 8038 Pepperwood Dr., Grand Blanc, MI (US) 48439

( * ) Notice: Subject to any disclaimer, the term of this patent is extended or adjusted under 35 U.S.C. 154(b) by 370 days.

(21) Appl. No.: 12/074,989

(22) Filed: Mar. 7, 2008

(65) Prior Publication Data
US 2009/0224561 A1    Sep. 10, 2009

(51) Int. Cl.
 B25J 15/06    (2006.01)
 A61B 17/52   (2006.01)
(52) U.S. Cl. ..................... 294/65.5; 606/106
(58) Field of Classification Search ............... 294/65.5, 294/3.6; 600/104–106, 11; 254/134.3 R, 254/134.3 FT; 606/106, 138, 200
See application file for complete search history.

(56) References Cited

U.S. PATENT DOCUMENTS

| | | | |
|---|---|---|---|
| 1,212,870 A * | 1/1917 | Zolper | 294/65.5 |
| 1,726,349 A | 8/1929 | Hartsough | |
| 2,087,034 A * | 7/1937 | Jameson | 294/65.5 |
| 2,095,976 A | 10/1937 | Foreman | |
| 2,321,355 A | 6/1943 | Berman | |
| 2,436,538 A | 2/1948 | Wing, Sr. | |
| 2,517,325 A | 8/1950 | Lamb | |
| 2,544,449 A | 3/1951 | Dunkelberger | |
| 2,623,774 A | 12/1952 | Hubbard | |
| 2,706,979 A | 4/1955 | Wallace | |
| 4,134,831 A * | 1/1979 | Dawson et al. | 588/303 |
| 4,572,561 A * | 2/1986 | Hale | 294/65.5 |
| 4,657,020 A | 4/1987 | Lifton | |
| 5,348,359 A | 9/1994 | Boozer | |
| 5,364,404 A | 11/1994 | Jaffe | |
| 7,608,038 B2 * | 10/2009 | Ginsberg | 600/104 |
| 2006/0284150 A1 * | 12/2006 | Spadaro et al. | 254/134.3 FT |

* cited by examiner

Primary Examiner—Dean J Kramer
(74) Attorney, Agent, or Firm—Dennis H. Lambert, Esq.

(57) ABSTRACT

A surgical magnetic retrieval tool for retrieving objects attractable by a magnet lost in a surgical cavity during a surgical procedure. The tool is a permanent magnet having a size and shape adapted to be placed in and moved through a surgical cavity to attract and hold the objects for retrieval of them from the cavity, and a flexible tether is attached to the magnet for supporting the magnet, pulling it through the cavity, and retrieving the magnet and objects attracted thereto from the cavity. In one form of the invention the magnet is a flexible magnetic sheet; in another form it is a sphere; in another form it is an oblate spheroid; and in another form it is a disc. The tool is disposable following use.

7 Claims, 2 Drawing Sheets

SURGICAL MAGNETIC RETRIEVAL TOOL

TECHNICAL FIELD

This invention relates generally to tools for retrieving objects lost in hard to reach or hard to see places. In particular, it relates to a magnetic retrieval tool for retrieving from surgical cavities objects having magnetic properties that may have become lost in the cavity during a surgical procedure.

BACKGROUND ART

It is not uncommon for objects to become lost in a surgical cavity during a surgical procedure. To minimize the risk of objects being left in a patient following a procedure, a count is made of objects used during the procedure and if the objects present after a procedure do not match the count a search of the surgical cavity is conducted to locate and retrieve any missing object or objects. Since there normally is a pool of blood in the cavity it is nearly impossible to visually locate any missing object, and especially small objects such as needles and the like. Accordingly, the search and retrieval normally is conducted by a surgeon or other medical professional placing his or her hands in the surgical cavity and searching by feel for the lost object. Large objects such as absorbent pads and the like may be relatively easy to locate and retrieve by this method, but it can be difficult to locate and retrieve smaller objects such as needles and the like. Further, there is substantial risk that the surgeon or other medical professional will be pricked or cut if the object being sought is sharp. Moreover, the cavity itself, or parts of the cavity, may be relatively small and difficult to access with the hands or fingers. This can be especially true in neurosurgical procedures where the surgical cavity is relatively small, and there are small crevices or spaces where an object may be located. If the items used during a surgical procedure cannot all be accounted for after the procedure, an X-ray and/or further surgical procedure may be required in order to locate and retrieve a missing item.

Various devices have been developed in the prior art for locating and/or retrieving metallic objects, i.e., objects made of a magnetic or magnetizable material, in body tissue and/or body cavities, including devices developed for use during a surgical procedure. Exemplary of such devices are those disclosed in U.S. Pat. Nos. 1,726,349, 2,321,355, 2,517,325, 2,706,979 and 4,657,020.

U.S. Pat. No. 1,726,349 to Hartsough discloses a rigid magnetic probe that is about the size of a lead pencil (16.5 cm long and 0.682 sq cm in cross section) for inserting in and moving along a body cavity or a wound to attract and retrieve metal objects. Because of its straight and rigid structure this device may be difficult to position in portions of a body cavity.

U.S. Pat. No. 2,321,355 to Berman discloses a relatively complex and expensive apparatus that uses an electromagnet for locating metal objects in body tissue. This apparatus locates the object but does not retrieve it. Moreover, because of its size it can not be easily placed in small cavities and crevices.

U.S. Pat. No. 2,517,325 to Lamb discloses a probe that incorporates a permanent magnet that may be moved into and out of a sheath to increase or reduce the magnetic field so that a metal object can first be oriented before it is attracted to the magnet and removed from the tissue. It is intended for use in retrieving magnetic splinters from the eye or skin of a patient, but is said to also be useful for removing metal splinters from food or electrical instruments.

U.S. Pat. No. 2,706,979 to Wallace discloses an electromagnetic surgical instrument for removing magnetic objects from body passages or cavities. It is a relatively complex and expensive rigid structure in the nature of a probe, and the magnetic field may be varied to enable manipulation of the object before it is removed, thereby preventing trauma to body tissue that might be caused by a sharp object.

U.S. Pat. No. 4,657,020 to Lifton discloses a permanent magnet on the end of an endoscope, with a shield that closes around a sharp object attracted to the magnet to prevent trauma to body tissue when the object is withdrawn from a body cavity. This device is designed and intended for insertion through a relatively large human body tract such as the gastrointestinal tract for retrieving objects that may have been swallowed by the patient.

The foregoing devices are relatively expensive and are intended for re-use.

Other, more simple and less expensive devices are known in the prior art wherein a magnet is carried on the end of a flexible tether for picking up articles made of a magnetic material. Exemplary of such devices are those disclosed in U.S. Pat. Nos. 1,212,870 and 2,623,774.

U.S. Pat. No. 1,212,870 to Zolper discloses a magnetic retrieval tool on a string. The magnet in this patent is a flat, rectangular plate with the string attached to the middle of the plate, and is intended to be suspended from the middle and slid along a floor surface to pick up and lift pins, needles and the like that have been dropped.

U.S. Pat. No. 2,623,774 to Hubbard discloses a toy hoist having a permanent magnet carried on the end of a string for picking up magnetic articles. The magnet is retractable through a tubular housing for dislodging the magnetic article from the magnet.

The foregoing devices are not designed or intended for use in a surgical environment to retrieve magnetic objects lost in a surgical cavity during a surgical procedure.

Accordingly, it would be desirable to have a simple and inexpensive surgical magnetic retrieval tool that can access small and hard to reach areas of a surgical cavity, wherein a small permanent magnet is affixed to the end of a flexible tether so that the magnet can be dropped into the surgical cavity and then pulled through it to attract and remove magnetic objects lost in the cavity during a surgical procedure.

DISCLOSURE OF THE INVENTION

The present invention comprises a simple and inexpensive surgical tool that can access small and hard to reach areas of a surgical cavity to attract and remove magnetic objects lost in the cavity during a surgical procedure, and which can be disposed of following use.

More specifically, the tool of the invention comprises a small permanent magnet affixed to the end of a flexible tether so that the magnet can be dropped into a surgical cavity and then pulled through the cavity to attract and remove magnetic objects lost in the cavity during a surgical procedure.

In one embodiment of the invention the magnet comprises a piece of flexible sheet material that provides a relatively large surface area for attracting objects and for shielding objects attracted to it, and whose shape enables it to enter small crevices and/or to relatively closely follow irregularly shaped portions of the surgical cavity.

In another embodiment, the magnet comprises solid rigid body in the shape of a small sphere, or oblate spheroid, or disc, or other shape that can readily enter small spaces and other areas of a surgical cavity that would not be readily accessible to conventional magnetic retrieval tools.

In both embodiments the magnet and tether are sterile, and the tether has sufficient length to extend well outside the surgical cavity during use. The tether can comprise a length of suture material or other flexible material such as a string or cord having sufficient strength for the intended purpose.

BRIEF DESCRIPTION OF THE DRAWINGS

The foregoing, as well as other objects and advantages of the invention, will become apparent from the following detailed description when taken in conjunction with the accompanying drawings, wherein like reference characters designate like parts throughout the several views, and wherein.

DETAILED DESCRIPTION OF THE BEST MODES FOR CARRYING OUT THE INVENTION

Figure 1:
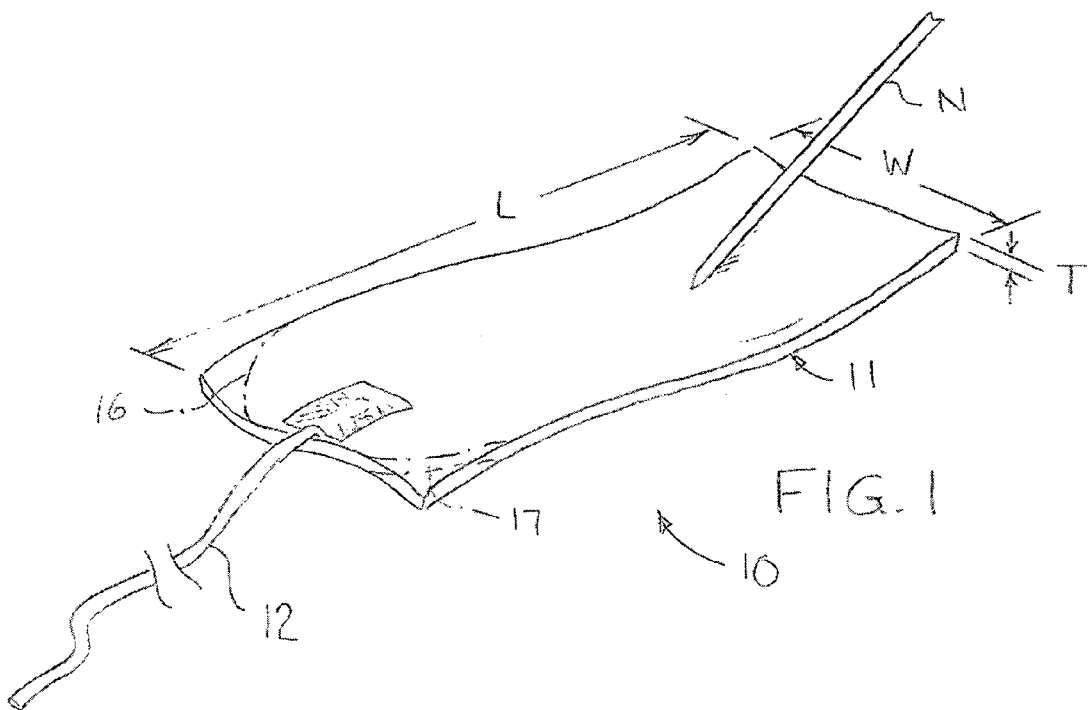
FIG. 1 is a top perspective view of a surgical tool in accordance with a first form of the invention.

A first form of the invention is indicated generally at 10 in FIG. 1 and comprises a flexible sheet or strip 11 of magnetic material having a flexible tether 12 affixed to one end thereof. To make the sheet, a powdered magnetic material is combined with a flexible thermoplastic binder and formed into a sheet by any suitable manufacturing process, such as by injection molding, for example, which is well suited to high volume applications. The flexible nature of the material enables it to be formed into intricate, tight-tolerance shapes.

There are four major families of permanent magnets: neodymium-iron-boron [Nd—Fe—B], samarium-cobalt [Sm—Co], alnico, and ceramic ferrite. Any of these can be used to make the magnetic sheet of the invention, but it is preferred to use Nd—Fe—B since of the materials listed this material produces the strongest magnetic field, with maximum energy product ranging from 26 megaGauss Oersteds (MGOe) to 52 MGOe. It has a combination of very high remanence and coercivity, and comes in a wide range of grades, sizes and shapes. With its excellent magnetic characteristics, abundant raw material and relatively low prices, Nd—Fe—B offers more flexibility than traditional magnet materials such as ceramic, Alnico and Sm-Co in achieving high efficiency, low cost and more compact devices. However, since this material is more prone to oxidation than the other magnet alloys, if it is to be exposed to humidity, chemically aggressive media such as acids, alkaline solutions, salts and harmful gases, it should be coated.

It is preferred to magnetize the sheet in a multi-polar arrangement, i.e., North-South-North-South, with the North and South poles spaced close together, e.g., anywhere from 2 poles per inch to 60 poles or more per inch. Since a higher pole density results in higher holding forces it is preferred to provide a relatively high pole density in the sheet of the invention, e.g. from about 25 poles per inch to about 60 poles per inch. The magnetic orientation is normally through the thickness.

The flexible sheet can be produced in various thicknesses, widths and lengths, with the preferred thickness T for a sheet magnet in accordance with the invention ranging from about 1/16" up to about 1/8", the preferred width W being about 1/2", and the preferred length L being about 3" when it is used in a relatively large surgical cavity such as might be formed in the abdomen, for example. If used in surgical cavities in the neck, head or spine, where the cavity typically is much smaller, the magnet may have length and width dimensions of about 1/2 cm and a thickness of only a couple of millimeters. It should be understood that the sheet of the invention could be made with other thicknesses, widths and lengths so long as it retains appropriate flexibility and size for the intended purpose. For example, as shown in the drawings the sheet has a greater width in relation to its length than the dimensions noted above, providing a larger surface area for attracting objects. Width and length dimensions W and L of about 1/2" and 3", respectively, would give the sheet of the invention dimensions comparable to the dimensions of a surgical pattie commonly used in surgical procedures.

Figure 3:
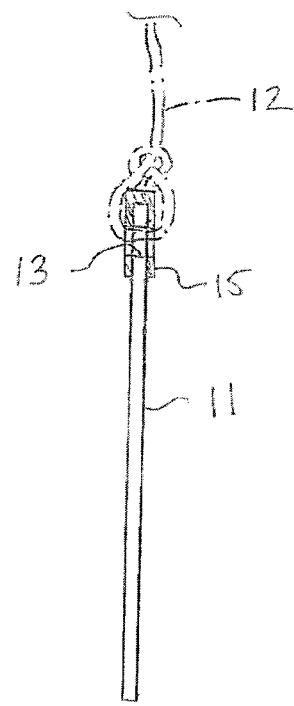
FIG. 3 is a side view in elevation of the tool of FIG. 2.

The tether 12 comprises a piece of flexible material such as a string, suture, or cord having a suitable length, preferably about 24", so that the tether extends well out of the surgical cavity during use, and is affixed to the end of the sheet 11 by gluing it to the sheet as shown in FIG. 1, tying it through an opening 13 as shown in FIG. 3, or by stapling it to the sheet (not shown), or by any other suitable means.

In use, the sheet 11 is simply dropped or placed into a surgical cavity, while the tether 12 is held in the hand of a surgeon or other medical professional. The sheet is then pulled or dragged through the cavity to attract and retrieve any metal objects lost in the cavity, such as needle N indicated in FIG. 1. The flexibility of the sheet enables it to generally follow the contours of the cavity, and its small thickness enables it to pass edgewise into small crevices.

Figure 2:
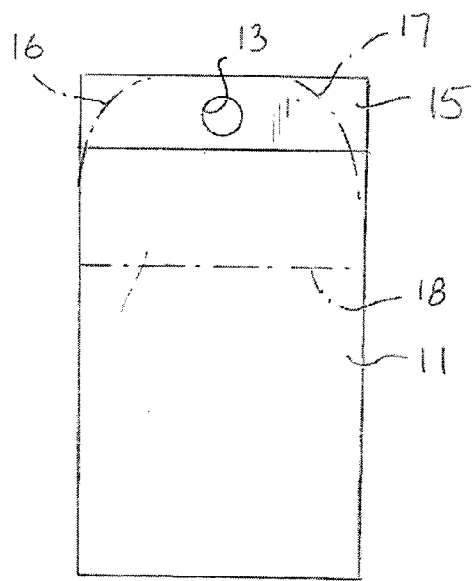
FIG. 2 is a top plan view of a modification of the tool of FIG. 1.

If desired, the leading end of the sheet can be covered with a non-magnetic material 15 as shown in FIGS. 2 and 3 so that any objects attracted to the sheet will be attracted to it at a position behind the leading end as the sheet is pulled through the surgical cavity. The leading end can be provided with rounded corners as indicated in dot-and-dash lines 16 and 17, and the non-magnetic cover 15 can extend over any desired length of the sheet, for example up to about half its length as indicated by the dot-and-dash line 18 in FIG. 2. Also, as depicted in FIG. 2, the sheet can have a greater width in relation to its length than the approximately 1 to 6 ratio of width to length in the preferred embodiment.

Figure 4:
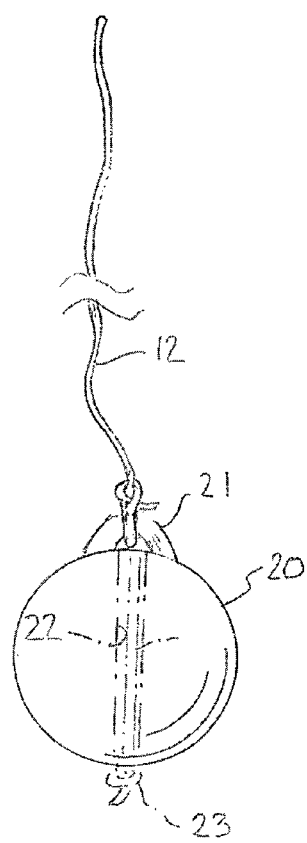
FIG. 4 is a greatly enlarged side view in elevation of a second form of the invention.
Figure 5:
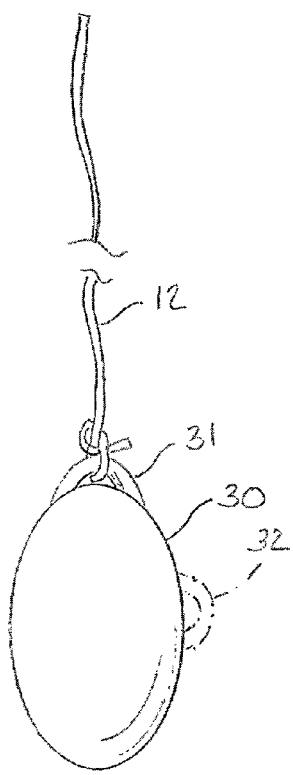
FIG. 5 is a greatly enlarged side view in elevation of a third form of the invention.
Figure 6:
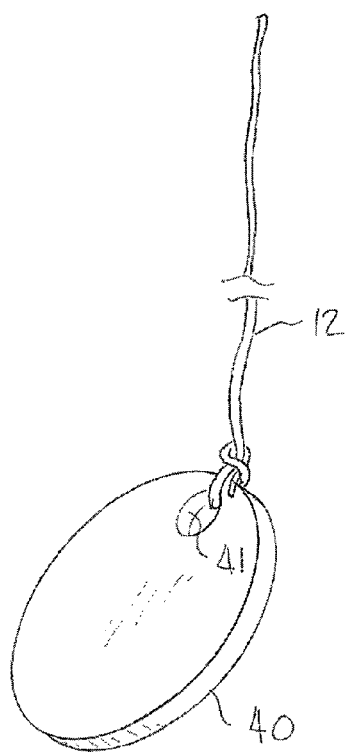
FIG. 6 is a greatly enlarged perspective view of a fourth form of the invention.

Variations of the invention are shown in FIGS. 4-6, wherein the magnet is a rigid body rather than a flexible sheet.

In FIG. 4 the magnet comprises a sphere 20, which preferably ranges in size from about 1/16" to about 5/8" in diameter, and is made of a suitable permanent magnet material such as those previously described, preferably neodymium-iron-boron. As with the first form of the invention, the magnet may have a diameter of only about 1/2 cm for use in very small spaces, and a larger diameter for use in larger spaces. The tether 12 is attached to the sphere by any suitable means, including a small eyelet 21 on the side of the sphere through which the tether is inserted and tied. Alternatively, the tether may be passed through a hole 22 extending through the sphere and tied into a knot 23 to prevent withdrawal of the tether from the hole, as indicated in dot-and-dash lines in FIG. 4, or by any other suitable means.

A further modification is shown in FIG. 5, wherein the magnet comprises an oblate spheroid or generally egg-shaped body 30 with a small eyelet 31 on one end for attachment of the tether 12. The eyelet may be on the side of the magnet rather than the end, as indicated by dot-and-dash lines at 32 in FIG. 5. The body 30 may have any suitable dimensions, preferably from about 1/16" to about 1" long and from about 2 mm to about 20 mm wide at its thickest point, but it may be much smaller (or larger, if appropriate) as in the first embodiment described.

A still further modification is shown in FIG. 6, wherein the magnet comprises a disc 40, preferably having approximately the thickness and diameter of a dime, although the disc can have any suitable size. For example, when used in association with head, spine or neck surgery the disc may have a diameter of 1/2 cm and a thickness of only 2 or 3 mm. The tether 12 is secured to the magnet in any suitable way, including tying it through a hole 41 near one edge of the magnet.

The magnet can have other shapes and sizes suitable for the intended purpose of attracting and retrieving objects from a surgical cavity, but it should be relatively small and have a streamlined shape that will enable it to move freely past body tissue, while at the same time having sufficient magnetic strength and size to attract and hold the objects.

Although particular embodiments of the invention are illustrated and described in detail herein, it is to be understood that various changes and modifications may be made to the invention without departing from the spirit and intent of the invention as defined by the scope of the appended claims.

What is claimed is:

1. A surgical magnetic retrieval tool for retrieving objects attractable by a magnet and lost in a surgical cavity during a surgical procedure, comprising:

a permanent magnet having a size and shape adapted to be placed in and moved through a surgical cavity to attract and hold said objects for retrieval of them from the cavity, said magnet comprising a flexible sheet of permanent magnet material; and a flexible tether attached to one end of the sheet for supporting it and pulling it through the surgical cavity.

2. A surgical magnetic retrieval tool as claimed in claim 1, wherein:

the sheet is approximately 1/16 inch to 1/8 inch thick, 1/2 inch wide, and 3 inches long.

3. A surgical magnetic retrieval tool as claimed in claim 2, wherein:

the permanent magnet material comprises a powdered magnetic material combined with a flexible thermoplastic binder.

4. A surgical magnetic retrieval tool as claimed in claim 3, wherein:

the powdered magnetic material comprises neodymium-iron-boron.

5. A surgical magnetic retrieval tool as claimed in claim 4, wherein:

the tether comprises a suture.

6. A surgical magnetic retrieval tool as claimed in claim 1, wherein:

the sheet has a length of from about 1/2 inch to about 3 inches, and a width of from about 1/4 inch to about 3/4 inch.

7. A surgical magnetic retrieval tool as claimed in claim 1, wherein:

the tool is disposable following use.

* * * * *